United States Patent [19]

Finnan et al.

[11] Patent Number: 4,710,519
[45] Date of Patent: Dec. 1, 1987

[54] PROCESS FOR PREPARING SPRAY DRIED ACETAMINOPHEN POWDER AND THE POWDER PREPARED THEREBY

[75] Inventors: Jeffrey L. Finnan, Southgate; Rudolph E. Lisa; Douglass N. Schmidt, both of Grosse Ile, all of Mich.

[73] Assignee: BASF Corporation, Parsippany, N.J.

[21] Appl. No.: 781,345

[22] Filed: Sep. 30, 1985

[51] Int. Cl.4 ................. A61K 31/735; A61K 31/165
[52] U.S. Cl. .................................... 514/629; 514/630; 424/489; 424/502
[58] Field of Search ....................... 514/629, 630, 276; 424/489, 502

[56] References Cited

U.S. PATENT DOCUMENTS

| 3,293,132 | 12/1966 | Stoyle et al. | 514/904 |
|---|---|---|---|
| 3,396,226 | 8/1968 | Cavalli et al. | 514/960 |
| 3,907,983 | 9/1975 | Seth | 514/276 |
| 3,914,430 | 10/1975 | Cannalonga et al. | 514/774 |
| 4,013,785 | 3/1977 | Weintraub et al. | 514/629 |
| 4,036,948 | 7/1977 | Kitamori et al. | 424/16 |
| 4,307,073 | 12/1981 | Nelson | 514/629 |
| 4,439,453 | 3/1984 | Vogel | 514/629 |
| 4,486,435 | 12/1984 | Schmidt et al. | 514/276 |
| 4,605,666 | 8/1986 | Schmidt et al. | 514/474 |

FOREIGN PATENT DOCUMENTS

| 1168156 | 5/1984 | Canada | 514/630 |
|---|---|---|---|
| 2416903 | 10/1975 | Fed. Rep. of Germany | 514/629 |

Primary Examiner—Ronald W. Griffin
Attorney, Agent, or Firm—Rupert B. Hurley, Jr.; David L. Hedden; Joseph D. Michaels

[57] ABSTRACT

The subject invention relates to a process for preparing acetaminophen powders by spray drying the acetaminophen in the presence of various excipients. Preferably a lubricant is incorporated into the acetaminophen powder during the spray drying process or after the spray drying process by passing the spray dried acetaminophen powder through a fluidized bed dryer which contains a lubricant.

14 Claims, No Drawings

PROCESS FOR PREPARING SPRAY DRIED ACETAMINOPHEN POWDER AND THE POWDER PREPARED THEREBY

BACKGROUND OF THE INVENTION

1. Field of the Invention

This invention relates to a process for preparing spray dried acetaminophen powder. The powder preferably contains a lubricant so that it will be directly compressible into tablets without the addition of further excipients. The invention also relates to the powders prepared by this process.

2. Description of the Prior Art

As is mentioned in U.S. Pat. No. 4,439,453, acetaminophen powder is generally prepared by a wet granulation technique. In this patent the acetaminophen granulation is prepared by charging acetaminophen powder and other ingredients to be used in the tablet to a fluidizer, fluidizing the mizture with warm air while spraying the mixture with an aqueous starch slurry, drying the mixture, adding a lubricant, and mixing the ingredients to uniformity. The process described in this patent is essentially a batch operation and is less coat effective than the process which will be described herein.

SUMMARY OF THE INVENTION

The subject invention relates to a continuous process for preparing acetaminophen powder which comprises spray drying an effective amount of an aqueous slurry of acetaminophen powder and a binder. Preferably, the aqueous slurry of acetaminophen and binder is spray dried in the presence of an adsorbent. The process is also preferably carried out in the presence of a lubricant which can be either added to the spray dryer chamber in a continuous process or to a fluid bed dryer in a continuous process or batchwise. Most preferably, the process is carried out such that the lubricant is added to the spray dryer or fluid bed dryer in a continuous process in the presence of heat. When the lubricant is added in the presence of heat, it is believed that a unique acetaminophen powder is prepared that is less susceptible to demixing when tableted than the acetaminophen powders disclosed in the prior art. The powders containing the lubricant are directly compressible into tablets without the addition of other excipients. They also have acceptable friability and hardness.

DESCRIPTION OF THE PREFERRED EMBODIMENTS

Typical binders (for example, see U.S. Pat. No. 3,293,132 at column 3, lines 29-54) that can be used include proteins such as gelatin, water-soluble derivatives of casein, e.g., sodium caseinate, and the like; water-soluble gums such as gum acacia, gum karaya, gum ghatti, tragacanth, and the like; cellulose, and water-soluble derivatives of celluloase such as methylcellulose, hydroxyethyl cellulose, sodium carboxymethylcellulose, and the like. For this purpose, use may furthermore be made of certain polyvinyl resins such as, for example, polyvinyl alcohol, polyvinyl pyrrolidine and the like. Preferably used are microcrystalline cellulose, and mixtures of microcrystalline cellulose and hydroxypropylmethylcellulose.

To prepare the aqueous slurry, the acetaminophen and binder are added to enough water to make a finished feed slurry having about 10 to 90 percent solids by weight, and, preferably, about 40 to 60 percent by weight solids.

The aqueous slurry containing the water-soluble vitamin and binder is preferably spray dried in the presence of an absorbent such as those disclosed in U.S. Pat. No. 3,914,430 at column 3, lines 43-68, which is hereby incorporated by reference. Preferably used as the absorbent is silicon dioxide, particularly silicon dioxide having a particle size of from 0.1 to 10.0 microns.

As was indicated previously, a lubricant is preferably a component of the powder and may be incorporated into the powder product by spray drying the acetaminophen and microcrystalline cellulose in the presence of the lubricant in addition to the absorbent. However, the preblending step to mix the absorbent and lubricant can be eliminated by adding the lubricant to the slurry and spray drying the slurry plus lubricant in the presence of only the absorbent.

Alternatively, the lubricant may be added to a fluid bed dryer, such as a vibrating bed dryer, where the spray dried powder is passed through to lubricate it. Preferably, the lubricant is added to the spray dryer or fluid bed dryer at a temperature sufficient to melt the lubricant. This will result in a more uniform distribution of the lubricant into the acetaminophen powder with the result that the powder will be less suceptible to demixing. Preferably used as the lubricant are stearic acid, magnesium stearate and mixtures thereof. However, other stearic acids salts may be used such as calcium stearate. Also, there can be used wax-like materials, for instance, wax-like saturated fatty acids, wax-like mixutres containing two or more saturated fatty acids or wax-like hydrogenated glyceride, in admixture with a metallic stearate and/or titanium dioxide such as are disclosed in U.S. Pat. No. 3,396,226 (column 3, lines 29-55) which is hereby incorporated by reference.

Additional excipients may also be used in preparing the subject powders. Although not used on a preferred basis because of nutiritonal factors, the subject powders may also contain carbohydrates such as sugars including lactose, sucrose, maltose, glucose, mannose, fructose, arabinose, and the like; non-sugars such as pectin, starch, and the like; and closely related polyhydric alcohols containing from 4 to 6 hydroxyl radicals such as mannitol, dulcitol, sorbitol, and the like.

The components described herein are used in amounts effective to produce a powder which will tablet. Those skilled in the art can determine what amounts are to be used based upon their own experience and the examples set forth herein. However, the components described herein are preferably added in amounts such that the final powder formed will contain at least 80 (preferably at least 90) percent by weight of acetaminophen, less than 15 (preferably less than 9) percent by weight of binder, 0.2 to 2 percent be weight of adsorbent, and 0.2 to 5 percent by weight of the lubricant and less than 3 percent of other excipients.

Any suitable spray dryer may be used to prepare the powders of this invention such as a vertical spray dryer equipped with a means of making droplets, such as a rotary atomizer operated between 10,000 and 35,000 rpm, preferably 18,000 to 25,000 rpm for a small dryer or suitable atomizer nozzles (such as high pressure, two- and three-fluid). The inlet temperature is maintained at 170° C. to 240° C., preferably 190° C. to 200° C., and the outlet temperature is a function of the inlet temperature and flow rate, generally between 80° C. to 110° C. From 0.5 to 2.5 percent by weight, based on the weight of the dry powder of silicon dioxide and from 0.5 to 5.0 percent of the lubricant is added to the spray dryer chamber, preferably at a point of negative pressure. The aqueous slurry of acetaminophen and binder is then spray dried to form a free-flowing, nonagglomerated powder.

Tablets from the powder are made by conventional methods. Useful tabletting aids are disclosed in Pharmaceutical Technology, July, 1980, pages 27–35, and 62.

The examples which follow will provide more details regarding how to practice the invention. In the examples, unless otherwise stated, all parts are by weight and all temperatures are in degrees Centigrade.

EXAMPLE 1

This example will illustrate the preparation of an acetaminophen powder by spray drying. This powder, however, did not contain a lubricant, and the lubricant was manually blended into the powder after spray drying.

An aqueous slurry containing 53 percent by weight solids was formed by adding 7,790 parts of acetaminophen, 432 parts of microcrystalline cellulose, and 164 parts of hydroxypropylmethylcellulose to water held in a stainless steel jacketed tank equipped with a turbin agitator. The aqueous slurry was sprayed into a 4' diameter vertical spray dryer at approximately 300 grams/minute using a rotary atomizing wheel at 23,000 rpm and an air inlet/outlet temperatures of 200° C./95–100° C. Silica was added by a screw feeder to the drying chamber, such that the finest composition is about:

| | |
|---|---|
| Acetaminophen | 92.9 percent |
| Hydroxymethylcellulose | 1.95 percent |
| Microcrystalline cellulose | 5.15 percent |
| Silica | <0.5 percent |

The resulting powder was blended for three minutes with 2 percent stearic acid as the lubricant.

EXAMPLE 2

Examples 2 illustrates a continuous process for preparing an acetaminophen powder by spray drying in which the lubricant has been added to the spray dryer.

An aqueous slurry, as described in Example 1, is spray dried except that a mixture of 2 parts stearic acid and 1 part silica is screw conveyed into the dryer chamber during the spray drying operation, such that the powder leaving the dryer contains the following:

| | |
|---|---|
| Acetaminophen | 90.1 percent |
| Hydroxypropylmethylcellulose | 1.9 percent |
| Microcrystalline cellulose | 5.0 percent |
| Stearic acid | 2.0 percent |
| Silica | 1.0 percent |

EXAMPLE 3

This example illustrates the preparation of a spray dried acetaminophen in which the lubricant is added to a fluidized bed dryer.

Again the aqueous slurry is spray dried as in Example 1 and 3000 grams of the unlubricated powder and 60 grams of stearic acid are charged to a fluid bed dryer. The bed was fluidized for 15 minutes with room temperature air. The temperature of the bed was then raised to 60° C. for 20 minutes at which time the powder was removed.

The powders for Examples 1–3 were all tabletted as shown below.

TABLE I

| Example | Tablet Weight (Gm) | Hardness S.C. Units | Friability[1] % |
|---|---|---|---|
| 1 | 0.581 | 15.6 | 0.47 |
| 2 | 0.586 | 14.9 | 0.29 |
| 3 | 0.581 | 13.9 | 0.47 |

[1]Loss after 125 revolutions (5 min.) in Vandercamp friabilator.

The results in this table show that the above processes were successful in preparing directly compressible acetaminophen tablets with adequate hardness and friabiltiy. It is preferable to add the lubricant to the spray dryer or to the fluidized bed so that the manual blending step can be eliminated. It is believed that by adding heat to the spray dryer or the fludized bed dryer sufficient to melt the lubricant, the resulting tablet is improved in that it will be less susceptible to demixing.

The embodiments of the invention in which an exclusive privilege or property is claimed are defined as follows:

1. A process of preparing a spray-dried acetaminophen powder, the process comprising:
   (a) spray-drying effective amounts of an aqueous slurry of acetaminophen and a binder; and
   (b) adding a lubricant to the acetaminophen and binder in the presence of heat so that the lubricant is not susceptible to demixing the the spray-dried acetaminophen.

2. The process of claim 1 wherein the amount of acetaminophen is such that the resulting powder contains at least 80 percent by weight of acetaminophen.

3. The process of claim 2 wherein the lubricant is melted after the lubricant is added to the spray-dried acetaminophen powder.

4. The process of claim 3 wherein during the spray-drying of the acetaminophen, the lubricant is added to the spray dryer while the temperature within the spray dryer is sufficient to melt the lubricant.

5. The process of claim 3 wherein the lubricant is mixed with the spray-dried acetaminophen powder is a fluid bed dryer, after which the acetaminophen and lubricant are heated to a temperature sufficient to melt the lubricant.

6. The process of claim 3 carried out in the presence of adsorbent.

7. The process of claim 5 carried out in the presence of an adsorbent.

8. The process of claim 7 wherein the lubricant is selected from the group consisting of stearic acid, magnesium stearate, and mixtures thereof.

9. The process of claim 8 wherein the powder comprises between 0.5 and 5.0 percent by weight of lubricant.

10. The process of claim 4 carried out in the presence of an adsorbant.

11. The process of claim 10 wherein the lubricant is selected from the group consisting of stearic acid, magnesium stearate, and mixture thereof.

12. The process of claim 11 wherein the powder comprises between 0.5 and 5.0 percent by weight of lubricant.

13. The process of claim 7 wherein the adsorbent is silicon dioxide.

14. The process of claim 12 wherein the adsorbent is silicon dioxide.

* * * * *